US012508068B2

(12) United States Patent
Ferzli

(10) Patent No.: US 12,508,068 B2
(45) Date of Patent: Dec. 30, 2025

(54) SURGICAL CAUTERY AND CUTTING DEVICE

(71) Applicant: George S Ferzli, Staten Island, NY (US)

(72) Inventor: George S Ferzli, Staten Island, NY (US)

( * ) Notice: Subject to any disclaimer, the term of this patent is extended or adjusted under 35 U.S.C. 154(b) by 377 days.

(21) Appl. No.: 18/202,457

(22) Filed: May 26, 2023

(65) Prior Publication Data

US 2024/0390060 A1 Nov. 28, 2024

(51) Int. Cl.

| | |
|---|---|
| ***A61B 18/14*** | (2006.01) |
| ***A61B 17/32*** | (2006.01) |
| ***A61B 18/00*** | (2006.01) |
| ***A61B 34/30*** | (2016.01) |

(52) U.S. Cl.

CPC .. *A61B 18/1482* (2013.01); *A61B 17/320016* (2013.01); *A61B 2018/00595* (2013.01); *A61B 2018/1422* (2013.01); *A61B 2034/302* (2016.02)

(58) Field of Classification Search

CPC ........ A61B 18/1482; A61B 17/320001; A61B 2034/302; A61B 2018/00595; A61B 2018/1422; A61B 2018/1417; A61B 2018/00994; A61B 2018/00607; A61B 2017/320074; A61B 2017/320075

USPC .......................................................... 606/41

See application file for complete search history.

(56) References Cited

U.S. PATENT DOCUMENTS

| | | | | |
|---|---|---|---|---|
| 3,234,356 | A | 2/1966 | Babb | |
| 4,655,216 | A | 4/1987 | Tischer | |
| 5,071,418 | A | 12/1991 | Rosenbaum | |
| 5,190,541 | A * | 3/1993 | Abele ................ | A61B 18/1442 606/49 |
| 5,254,115 | A | 10/1993 | Bhatta et al. | |
| 5,312,391 | A | 5/1994 | Wilk | |
| 5,376,089 | A | 12/1994 | Smith | |
| 5,718,703 | A | 2/1998 | Chin | |
| 5,800,449 | A * | 9/1998 | Wales ................ | A61B 18/1447 606/205 |
| 6,328,736 | B1 | 12/2001 | Mulier et al. | |
| 6,551,313 | B1 | 4/2003 | Levin | |
| 7,118,584 | B2 * | 10/2006 | Griego ............... | A61B 18/1492 606/171 |
| 8,048,073 | B2 * | 11/2011 | Nakamura ......... | A61B 18/1492 606/41 |

(Continued)

FOREIGN PATENT DOCUMENTS

| | | | |
|---|---|---|---|
| EP | 2005912 | B1 | 5/2016 |
| EP | 2983598 | B1 | 3/2022 |

*Primary Examiner* — Beverly M Flanagan

(74) *Attorney, Agent, or Firm* — Jordan and Koda, PLLC; Steven P. Koda, Esq.

(57) ABSTRACT

A minimally invasive surgical instrument combines a cautery tool and knife tool for performing operative actions, including tissue destruction, coagulation, dissection, and transection. An elongated body has a channel extending in a longitudinal direction to a distal end. The knife tool is situated in the channel and movable along the channel. The cautery tool includes a conductor electrically coupled to a cautery tip. The cautery tip includes a resistive element with a through opening in axial alignment with the channel. The knife tool has a retracted position in which a blade of the knife tool is unexposed, and a fully extended position in which the blade is exposed distal to the through opening.

20 Claims, 12 Drawing Sheets

(56) References Cited

U.S. PATENT DOCUMENTS

| | | | | |
|---|---|---|---|---|
| 8,820,605 | B2 | 9/2014 | Shelton, IV | |
| 8,945,163 | B2 | 2/2015 | Voegele et al. | |
| 8,992,424 | B2 * | 3/2015 | Orbay ................ | A61B 1/00105 600/183 |
| 9,962,222 | B2 | 5/2018 | Brustad et al. | |
| 10,064,675 | B2 | 9/2018 | Rencher et al. | |
| 10,299,771 | B2 | 5/2019 | Baldwin | |
| 10,722,297 | B2 | 7/2020 | Ravikumar et al. | |
| 11,607,265 | B2 | 3/2023 | Bonn | |
| 11,890,049 | B2 * | 2/2024 | Batchelor ............ | A61B 17/295 |
| 2007/0118135 | A1 | 5/2007 | MAnsmann | |
| 2010/0016853 | A1 | 1/2010 | Burbank | |
| 2023/0081874 | A1 * | 3/2023 | Mchenry ................ | A61B 34/30 606/51 |
| 2023/0082915 | A1 | 3/2023 | Chassot et al. | |
| 2023/0093858 | A1 | 3/2023 | Roman et al. | |
| 2023/0200888 | A1 * | 6/2023 | Fry .................... | A61B 18/1447 606/41 |
| 2023/0248418 | A1 * | 8/2023 | Rich .................. | A61B 18/1206 606/41 |

* cited by examiner

SURGICAL CAUTERY AND CUTTING DEVICE

BACKGROUND OF THE INVENTION

The present invention relates to manual and robotic surgical cautery and cutting tools, and methods for minimally invasive surgery using same.

Minimally invasive surgery is any technique involved in surgery that does not need a large incision. Robotic surgery may be associated with each of open surgery and minimally invasive surgery. Robotic surgery, also called robot-assisted surgery, allows medical practitioners to perform complex procedures with more precision, flexibility and control than is possible using conventional surgical techniques. An "open" surgery means the cutting of skin and tissues so that the surgeon has a full view of the structures or organs involved.

Various types of minimally invasive procedures include laparoscopic, endoscopic, arthroscopic, bronchoscopic, thoracoscopic, cystoscopic, gastroscopic, hysteroscopic, laryngoscopic, sigmoidoscopic, and colonoscopic procedures.

Laparoscopic surgery is conducted via the peritoneal cavity by percutaneous insertion of appropriate instruments through the abdominal wall. By manipulation of the instruments while viewing the surgical site through a laparoscope, surgery may be performed on the gallbladder, the kidneys, liver and large bowel, for instance.

Endoscopic surgery in general, and laparoscopic surgery in particular are recognized to have considerable advantages over open surgery because of the avoidance of large incisions and the discomfort, long and expensive hospital stay, and extended period of incapacity required by such incisions. Endoscopic procedures instead employ a few small penetrations of the body, which lessen the patient's discomfort, and reduce the time and expense of the hospital stay and the patient's period of incapacity.

Open and minimally invasive procedures often involve cutting and connecting bodily tissue including organic materials, musculature, connective tissue and vascular conduits. Bodily tissue typically is cut during a surgical procedure. As bodily tissue is highly vascularized there tends to be bleeding. Surgeons have long sought surgical instruments and methods that slow or reduce bleeding during surgical procedures.

Medical practitioners use electrocauterization to control bleeding from small blood vessels, remove diseased tissue, destroy abnormal tissue, prevent uncontrolled bleeding, and remove small skin growths and areas of damaged skin. Electrocautery is one form of electrosurgery. Electrocautery and electrocauterization as used herein are distinguished from AC-type (alternating current type) electrosurgery. AC-type electrosurgery is the surgical application of high-frequency electricity to cause the thermal tissue effects of vaporization, desiccation, coagulation and fulguration. It is not synonymous with electrocautery as used herein. AC-type electrosurgery includes monopolar electrocaurery (having a passive return electrode at the patient), and bipolar electrocautery (having a return path at the device tip.)

Electrocautery is a form of direct transference of heat to the tissue. Instead of passing electrical current through the tissue, low-voltage, high-amperage, direct or alternating current is used to heat a resistive element, which is applied to the tissue. The resulting effect depends on the tissue. Direct application to tumor leads to destruction of tumor cells, whereas application to vessels results in hemostasis. Electrocautery is most commonly used when high-frequency electrosurgery is contraindicated.

An electrocautery device can deliver heat at a single temperature or range of temperatures, between 100° C. and 1200° C. Surgeons consider the histologic properties of the tissue to be treated, the area and depth of destruction desired, possible complications, and capabilities of the different electrocautery tools. A common principle of all electrosurgical procedures is to use the least amount of power possible to achieve the desired effect, limiting damage to the adjacent tissue.

Electrosurgical instruments are available that use electrical energy to perform electrocautery. Typically, electrosurgical instruments are hand instruments. One or more electrodes are configured to be supplied with electrical energy from an electrosurgical unit including a power supply. The electrical energy can be used to coagulate, fuse, or cut tissue to which it is applied. Advantageously, application of electrical energy to tissue tends to stop bleeding of the tissue. A shortcoming of using electrosurgical waveforms for "cutting", however, is a poor ability to transect tissue. This is intentional as many surgeons need much more coagulation capability.

Some medical procedures require cauterization of certain vessels in order to permanently prevent the passage of blood or other substances through those vessels. In gallbladder surgery, isolation of the gallbladder often requires cauterization of the cystic artery, the artery which carries blood to the gallbladder. Cauterization of the vessels in the mesentery, the fold attaching the bowel to the body wall, is needed during bowel resection to provide surgical access to the bowel. Cauterization is also frequently used to seal the vas deferens in vasectomy, and in tubal ligation to seal the fallopian tubes to block the passage of sperm and egg, respectively. Cauterization is also frequently used for inguinal or ventral and incisional hernia procedures.

SUMMARY OF THE INVENTION

The surgical instrument of the present invention combines a cautery tool and a knife tool allowing the surgeon to perform diverse operative actions on blood and tissue, including blood coagulation and tissue destruction, dissection, and transection. The instrument is particularly adapted for minimally invasive surgery, although it may be used in open surgery. The surgical instrument includes an elongated body extending longitudinally in an axial direction and having a first channel extending in the longitudinal direction to a distal end of the elongated body. The knife tool includes a shaft and a distal portion having a blade. The knife tool is situated in the first channel and is movable along the first channel. In a specific embodiment the first channel is a through channel extending longitudinally in an axial direction. A blade is adapted for performing a cutting action consisting of mechanically cutting by applying physical stress. The blade has a cutting edge with a physical sharpness adapted for performing the cutting action against tissue.

The cautery tool including a conductor and a cautery tip electrically coupled to the conductor. The conductor is embedded in the elongated body. In some embodiments the elongated body includes a second channel in which the conductor is situated. The conductor is insulated in the elongated body so as to be electrically isolated from the knife tool. The cautery tip is positioned at the distal end of the elongated body and electrically coupled to the conductor. The conductor and cautery tip has a cautery-off state and a cautery-active state. During the cautery-active state, the cautery tip is energized to provide heat for performing any one or more of a cauterizing, coagulating, and dissecting action.

The knife tool is movable within the first channel between a retracted position and a fully extended position. The cautery tip has a through opening aligned with the first channel of the elongated body. The cutting edge of the knife tool is unexposed when the knife tool is in the retracted position. Preferably, the distal tip of the knife tool is proximal to the distal end of the first channel when the knife tool is n the retracted position. In other embodiments, the distal tip of the knife tool is in the through opening, but proximal to the distal end of the through opening, when the knife tool is on the retracted position. The distal portion of the knife tool, including the cutting edge, travels through the through opening to be exposed distal to the through opening when the knife tool is moved from the retracted position to the fully extended position. Specifically, the cutting edge of the knife tool is exposed distal to the distal end of the cautery tip when the knife tool is in the fully extended position.

In some embodiments the surgical instrument includes a proximal base. In various embodiments the proximal base is formed as a hand grip, one or more finger grips, or a robotic arm.

There are various preferred embodiments of a knife position-setting structure, which determines the position of the knife tool along the first channel of the elongated body. The knife tool is advanced and retracted in the axial direction along the first channel. The knife position-setting structure is embodied by the elongated body, the knife tool, and the proximal base in various embodiments. For example, an access structure which can be grasped by the surgeon, is accessible at the proximal end of the knife tool or the proximal end of a sled coupled to the knife tool. A groove or track is formed at the proximal end of the elongated body or at the proximal base. The access structure is moved forward or backward along the axial direction of the groove to move the knife tool. In some embodiments, the groove has multiple notches to lock the knife tool into position at the retracted position, the fully extended position, or at an intermediate extended position.

In another preferred embodiment, the knife position-setting structure includes a ratchet gear and pawl at the proximal base. A first trigger is pulled to rotate the ratchet gear and advance the knife tool along the first channel. The pawl locks the ratchet gear in position with the knife advanced. A second trigger releases the pawl. The ratchet gear is spring biased to return the knife tool to the retracted position. An advantage for this embodiment for a hand-held instrument is that one hand can grip and operate the instrument. More specifically a single finger can be used to pull the first or the second trigger to advance or retract the knife tool relative to the first channel and through opening.

In various embodiments the cautery tip is configured as a spatula, ball, L-hook, J-hook, or other shape. For a hook embodiment the cautery tip through opening extends through a ledge portion. For the spatula and ball tips the through opening in the cautery tip is continuous with the first channel of the elongated body. For the hook-shaped tip embodiments there is an open space region between a distal end of the first channel of the elongated body and the through opening at the ledge portion. Accordingly for the hook embodiments, the distal tip of the knife tool travels through the open space region as the knife tool travels from the retracted position to the fully extended position. The surgical instrument is configured so the knife tool's cutting edge is unexposed within the first channel while the knife tool is in the retracted position. The surgical instrument is configured so the knife tool's cutting edge is exposed in the open space region while the knife tool is in an intermediate extended position. The surgical instrument is configured so the knife tool's cutting edge is exposed distal to the distal side of the ledge portion while the knife tool is in the fully extended position.

The surgical instrument in accordance with embodiments of the present invention is useful, for example, in incarcerated inguinal hernia procedures and abdominal wall hernia procedures, in which the ring of the defect needs to be cut to enlarge the defect so the surgeon can reduce the incarcerated contents. The instrument also is useful as an alternative to the scissor in dividing adhesions very close to the intestines. The instrument also is useful for any procedures where an incision is needed (without heat/energy) followed by the need for cauterization. In a gallbladder procedure, the surgical instrument is useful for example after clipping the cystic duct and cystic artery. The surgeon can use the hook tip and knife tool's cutting edge to cut the cystic duct and the cystic artery and then continue with a hook cautery dissection. This has an advantage over the multiple step procedure of inserting and removing tools from the laparoscopic incision. For example, when using scissors, the surgeon needs to removery the cautery tool, then get and insert the scissors, then cut with the scissors, then remove the scissors, then re-inert the cautery tool. The present invention eliminates an exchange of instruments through the incision. This is particularly advantageous for a robotic surgical procedure where a knife is needed, such as for choledochotomie, pyloromyotomy, or an excision biopsy of a solid tumor, to avoid a cautery artifact.

DETAILED DESCRIPTION OF THE PREFERRED EMBODIMENTS

In the following description, for purposes of explanation and not limitation, specific details may be set forth to provide a thorough understanding of the present invention. However, it will be apparent to one skilled in the art that the present invention may be practiced in other embodiments that depart from these specific details. Detailed descriptions of well-known components are omitted so as not to obscure the description of the present invention.

Figure 1:
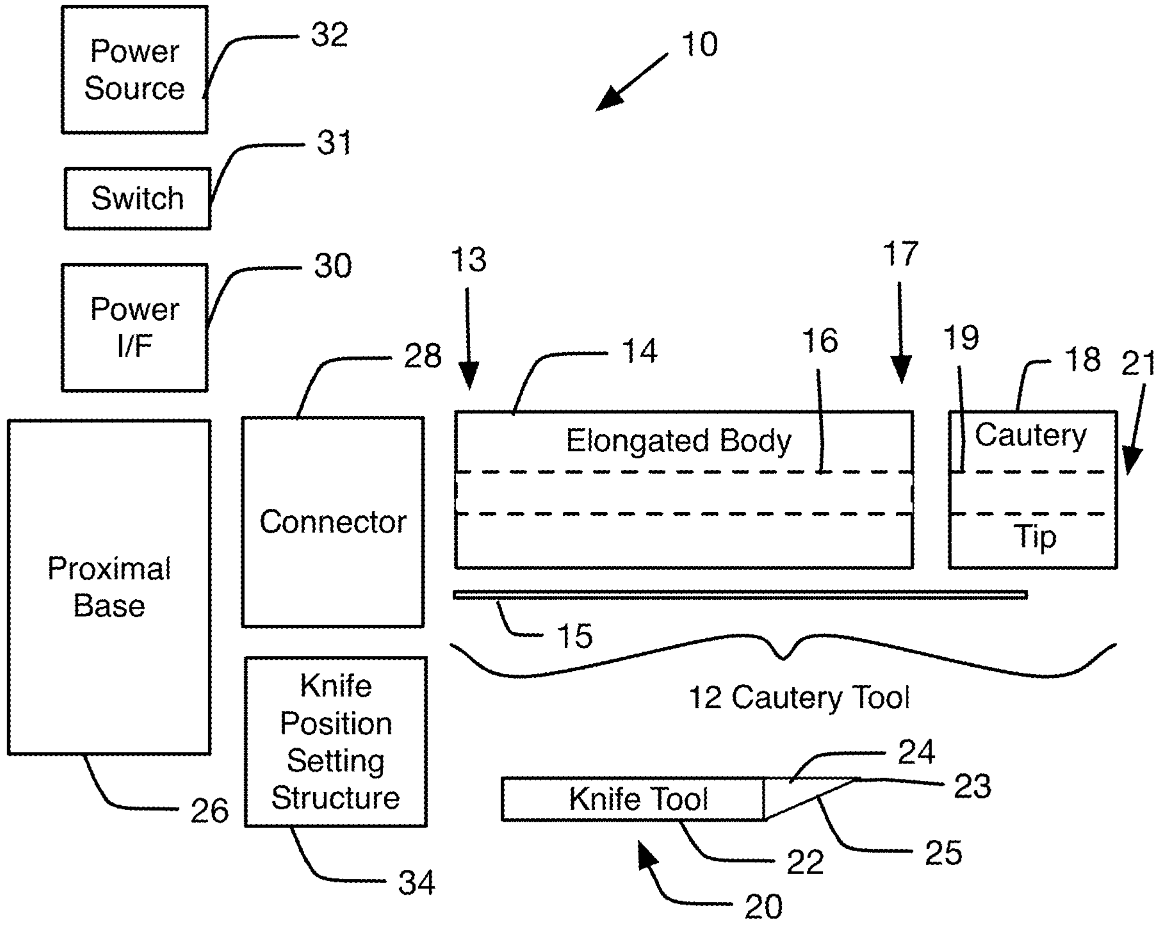
FIG. 1 is a block diagram of a surgical instrument, in accordance with an embodiment of the present invention.

Referring to FIG. 1, a surgical instrument 10 is illustrated in accordance with an embodiment of the present invention. The surgical instrument includes a cautery tool 12, an elongated body 14, a knife tool 20, and a proximal base 26. The cautery tool 12 includes a conductor 15 and a cautery tip 18. The elongated body 14 has a channel 16, which preferably extends through the elongated body 14 from a proximal end 13 to a distal end 17. The cautery tip 18 has a through opening 19 axially aligned with the channel 16. The cautery tip 18 is formed separately from the elongated body and may be removably attached and replaced, or be permanently affixed. In other embodiments the elongated member 14, conductor 15, and cautery tip 18 are a single integrated member.

The knife tool 20 includes a shaft 22 and a distal portion 24. In some embodiments the knife tool 20 extends a partial length of the elongated member 14. In other embodiments the knife tool 20 extends to a proximal end of the elongated member 14 when the knife tool is retracted. Is still other embodiments, the knife tool extends proximal to the proximal end of the elongated body 14 into the proximal base 16. The distal portion 24 of the knife tool has a cutting edge 25. The knife tool 20 is situated in the channel 16, and is movable between a retracted position and a fully extended position. In an exemplary embodiment the cutting edge 25 can have a standard #11 blade shape or a standard #15 blade shape. In an exemplary embodiment channel 16 has a diameter of 5 mm or less and the shaft 22 has a cross sectional diameter of 2-3 mm. In another exemplary embodiment the channel 16 has a diameter of less than 10 mm and the shaft 22 has a cross sectional diameter of 8 mm. The specific diameter of the channel 16 and knife shaft 22 can differ according to different embodiments and surgical needs. The diameter of the cautery tip 18 through hole 19 preferably is the same as the diameter of the channel 16. In other embodiments the cross-sectional shape of the through hole 19 has the shape of the cross section of the distal portion 24, or a cutting edge portion of the knife tool 20. For example, the cross-sectional shape of the through hole 19 may differ from the cross sectional shape of the shaft 22. In such embodiment, the distal portion 24 may extend into the through opening 19 and the cutting edge 25 extend beyond the distal end of the through opening 19. In effect the differing cross-sectional shape of the through hole 19 limits the potential fully extended position of the knife tool 20.

The surgical instrument 10 includes the proximal base 26 to which the elongated body 14 is removably attached by a connector 28. A power interface 30 is situated at the proximal base 26, connector 28, or elongated body 14. A power source 32 is coupled to the power interface 30 to drive the cautery tool 12 into an active state, in which the cautery tip 18 is heated for performing a cauterizing action, such as to provide coagulation of a blood vessel, dissection of tissue, or destruction of tissue. In some embodiments the power source is coupled to the power interface by a wire and adapter. A switch 31 at the power source turns power on or off to use the instrument 10 in the cautery-off state or cautery-on state. In other embodiments the power source includes batteries situated in the proximal base 26. The switch 31 is situated at the proximal base 26 and turns power on or off to use the instrument 10 in the cautery-off state or cautery-on state. In various embodiments the switch 31 is located at the power supply 32, proximal base 26, or elongated body 14. In various embodiments the switch 31 is wired to be between the power source 32 and power interface 30, between the power interface 30 and the connector 28, or between connector 28 and the conductor 15.

The surgical instrument 10 also includes a knife position-setting structure 34. The knife position-setting structure 34 is manipulated to move the knife tool 20 along the channel 16 between the retracted position and a fully extended position. In some embodiments, the knife position-setting structure 34 is integrally formed toward or at a proximal end of the knife tool 20. In other embodiments, the knife position-setting structure 34 includes a separate member axially located at least partially within the channel 16 and aligned with the shaft 22 of the knife tool 20. The knife tool 20 preferably is locked in the retracted position or fully extended position. In some embodiments, the knife position-setting structure 34 also can lock the knife tool 20 in an intermediary position between the retracted position and the fully extended position. In the retracted position the knife tool 20 is unexposed-meaning that the distal end 23 of the knife tool remains proximal to the distal end 21 of the through opening 19 of the cautery tip, or for some embodiments meaning that the distal end 23 of the knife tool 20 remains proximal to the distal end 17 of the channel 16 of the elongated body 14. In the fully extended position distal tip 23 of the knife tool 20 extends distal to the distal end 21 of the through opening 19 of the cautery tip 18. In particular, the cutting edge 25 is exposed beyond the distal end 21 of the through opening 19, so as to allow for a cutting action in the space beyond the distal end 21 of the cautery tip 18.

The surgical instrument 10 may be embodied in various cautery tip 18 configurations. The spatula 18" is electrically resistive so as to heat up during the cautery-on state. FIGS.

Figure 2A:
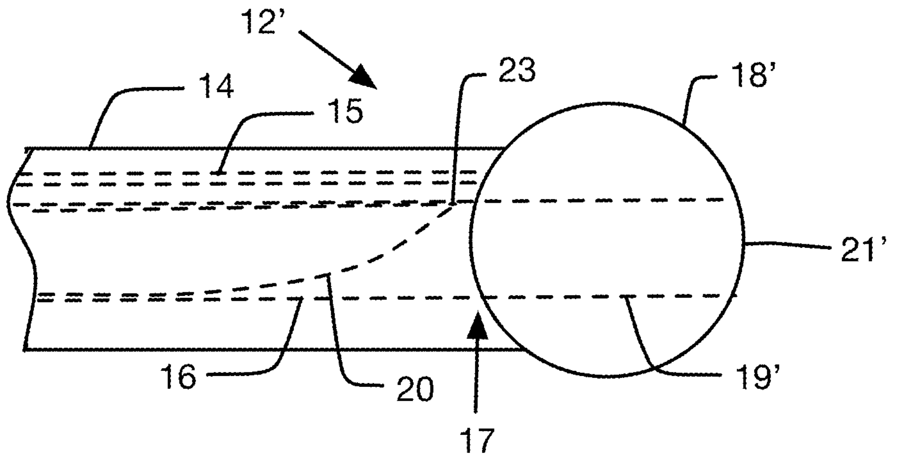
FIGS. 2A and 2B are diagrammatic views of a portion of a cautery tool and the knife tool with the knife tool in the retracted position (FIG. 2A) and the fully extended position (FIG. 2B) for a ball shaped cautery tip.
Figure 2B:
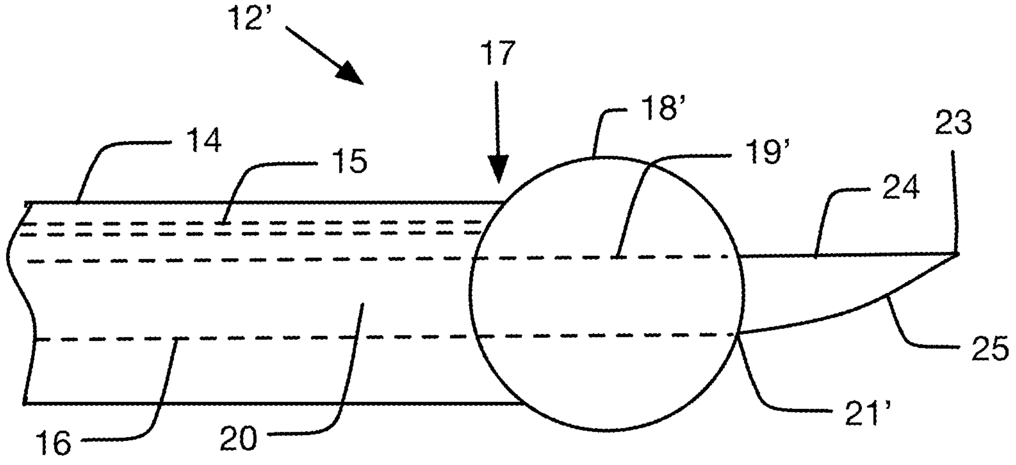

2A and 2B show an embodiment of the cautery tool 12', in which the cautery tip 18 is configured as a ball 18' having a through opening 19' with a distal end 21'. FIG. 2A shows the knife tool 20 in the retracted position, in which the distal end 23 of the knife tool 20 is proximal to the distal end 17 of the channel 16 of the elongated body 14. FIG. 2B shows the knife tool 20 in the fully extended position, in which the distal end 23 of the knife tool 20 is distal to the distal end 21' of the through opening 19' of the cautery tip 18'. The knife tool 20 is locked into the fully extended position allowing the surgeon to perform a cutting action. In particular the cutting edge 25 of the knife tool is exposed to allow a cutting action against tissue distal to the cautery tip 18'.

Figure 3A:
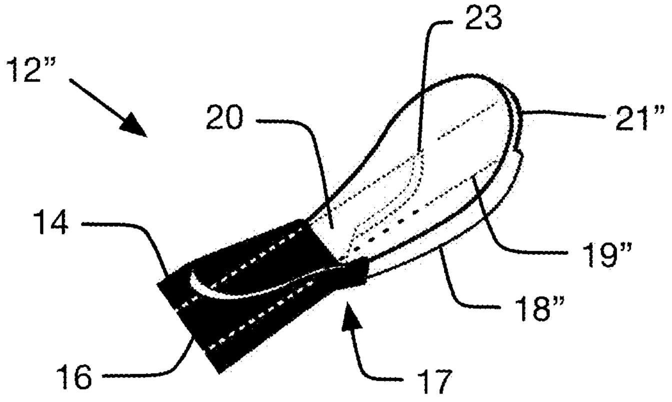
FIGS. 3A and 3B are diagrammatic views of a portion of a cautery tool and the knife tool with the knife tool in the retracted position (FIG. 3A) and the fully extended position (FIG. 3B) for a spatula shaped cautery tip.
Figure 3B:
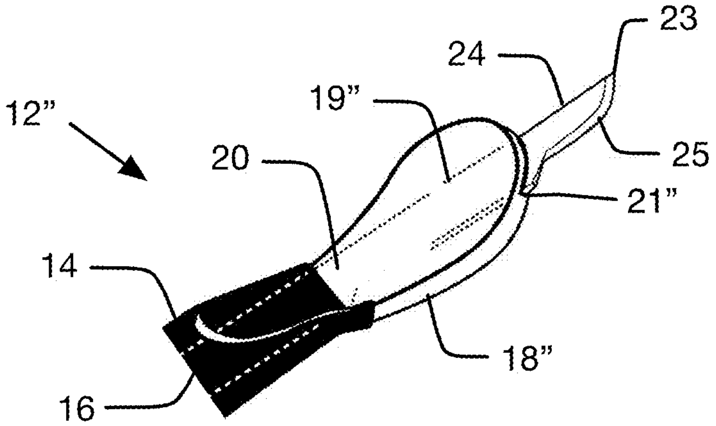

FIGS. 3A and 3B show an embodiment of the cautery tool 12", in which the cautery tip 18 is configured as a spatula 18" having a through opening 19" with a distal end 21". The spatula 18" is electrically resistive so as to heat up during the cautery-on state. FIG. 3A shows the knife tool 20 in the retracted position, in which the distal end 23 of the knife tool 20 is proximal to the distal end 17 of the channel 16 of the elongated body 14. FIG. 3B shows the knife tool 20 in the fully extended position, in which the distal end 23 of the knife tool 20 is distal to the distal end 21" of the through opening 19" of the cautery tip 18". The knife tool 20 is locked into the fully extended position allowing the surgeon to perform a cutting action. In particular the cutting edge 25 of the knife tool is exposed to allow a cutting action against tissue distal to the cautery tip 18".

Figure 4A:
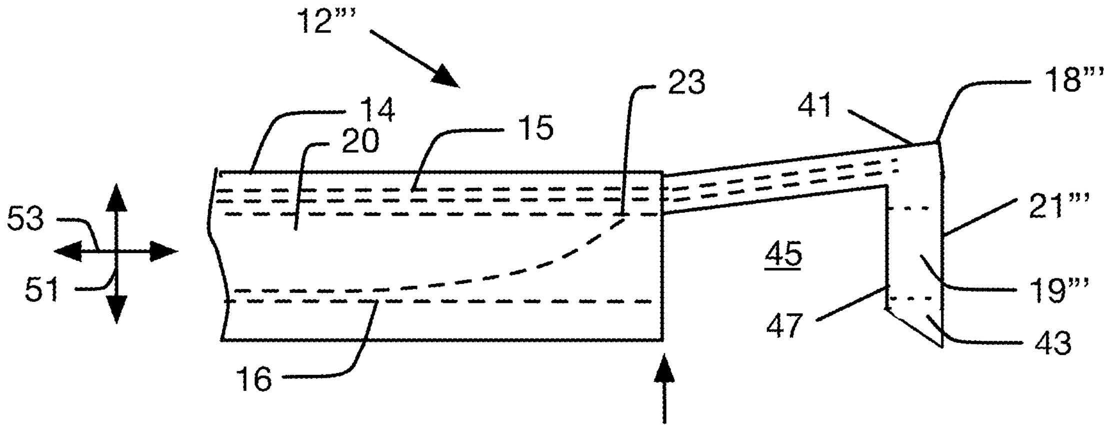
FIGS. 4A, 4B, and 4C are diagrammatic views of a portion of a cautery tool and the knife tool with the knife tool in the retracted position (FIG. 4A), intermediate extended position (FIG. 4B), and the fully extended position (FIG. 4C) for an L-hook shaped cautery tip.
Figure 4B:
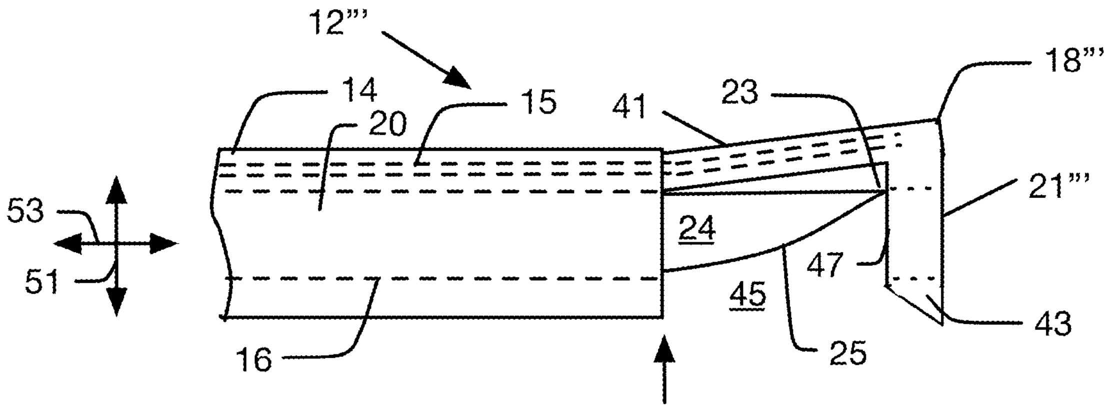
Figure 4C:
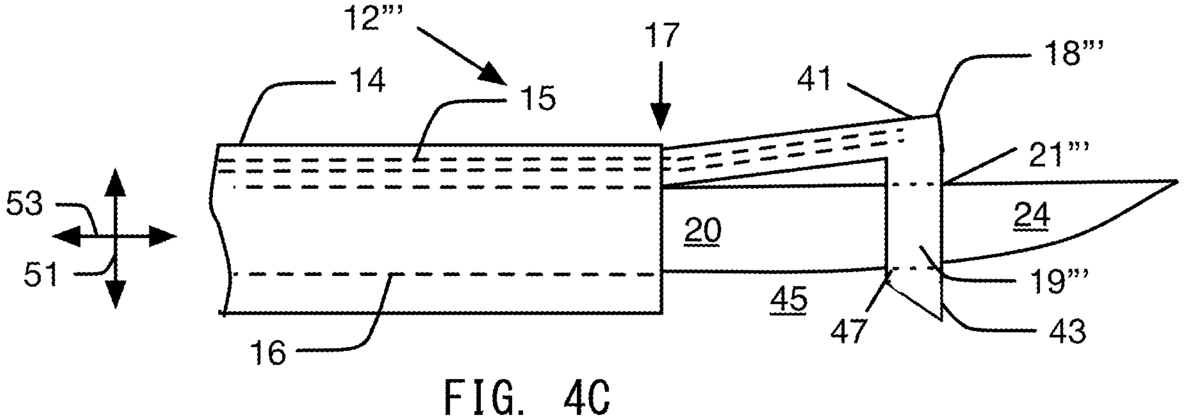

FIGS. 4A, 4B, and 4C show an embodiment of the cautery tool 12'", in which the cautery tip 18 is configured as an L-hook 18'" having a through opening 19'" with a distal end 21'". In some embodiments the entire cautery tip 18'" is a resistive element that heats up during the cautery-on state in response to receiving a current via the conductor 15. The L-hook 18'" has an arm portion 41 and a ledge portion 43. In some embodiment only the ledge portion 43 is electrically resistive so as to heat up during the cautery-on state. The ledge portion 43 includes the through opening 19'". The ledge portion 43 extends transverse to the axial direction 53 of the elongated body 14. In other embodiments the ledge portion 43 may extend away from the transverse axis 51 such as at any angle between plus or minus 45 degrees off the transverse axis 51. In still other embodiment the ledge portion may have a curved proximal surface. Because the ledge portion 43 is separate from and distal to the distal end 17 of the channel 16 of the elongated body 14, there is an open space region 45 between the distal end 17 of the channel 16 and the proximal side 47 of the ledge portion 43. Accordingly, the knife tool 20 as it is moved distally along the channel 16 may expose the cutting edge 25 in the region 45. FIG. 4A shows the knife tool 20 in the retracted position, in which the distal end 23 of the knife tool 20 is is proximal to the distal end 17 of the channel 16 of the elongated body 14. The cutting edge 25 is not exposed.

FIG. 4B shows the knife tool 20 in an intermediate extended position between the retracted position and the fully extended position. In the intermediate extended position the cutting edge 25 of the distal portion 24 of the knife tool 20 is exposed in the region 45 proximal to the ledge portion 43 of the cautery tip 18". In some embodiments there are various intermediate positions in which a portion of the cutting edge 25 is exposed in region 45. The distal end 23 may be located in the region 45 or within the through opening 19'" in an intermediate extended position. In some embodiments, there is only one intermediate position at which the knife tool's position can be locked. In other embodiments, there are multiple locking positions corresponding to multiple intermediate extended positions. Of significance is that the cutting edge 25 is exposed in the region 45 allows for cutting of tissue located in region 45. For example, the cutting edge 25 can cut through tissue aligned with the through opening 19'". In some embodiments, the knife tool 20, including the cutting edge 25, is moved in the axial direction 53 without being locked in position, so as to cut through tissue aligned with the through opening 19'" as the distal end 23 of the knife tool 20 moves into and/or through the through opening 19'".

FIG. 4C shows the knife tool 20 in the fully extended position, in which the distal end 23 of the knife tool 20 is distal to the distal end 21'" of the through opening 19'" of the cautery tip 18'". The knife tool 20 is locked into the fully extended position allowing the surgeon to perform a cutting action. In particular the cutting edge 25 of the knife tool is exposed to allow a cutting action against tissue distal to the cautery tip 18'".

Embodiments with 1St Knife Position-Setting Structure

Figure 5:
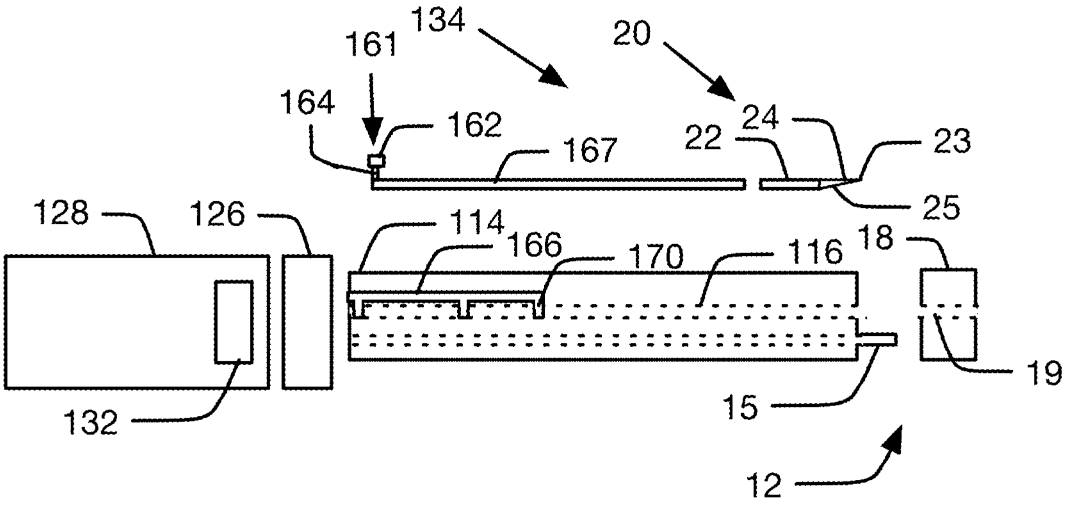
FIG. 5 is an exploded diagrammatic view of a surgical instrument, in accordance with a first embodiment of the present invention.
Figure 6:
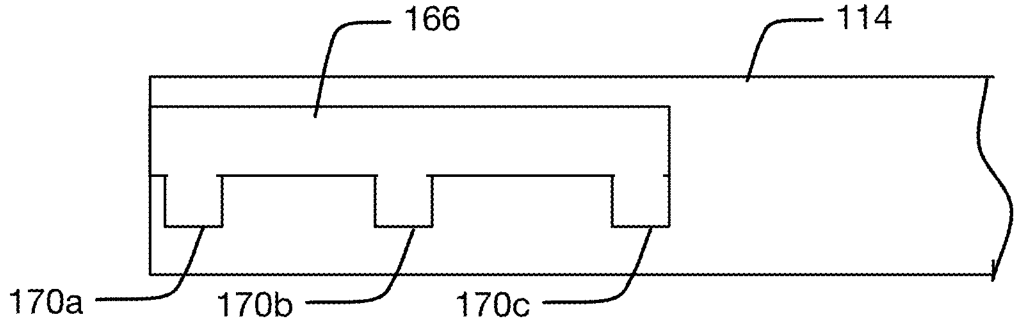
FIG. 6 is a diagrammatic view of the proximal end of the elongated body of the cautery tool of FIG. 5, in accordance with the first embodiment of the present invention.
Figure 7:
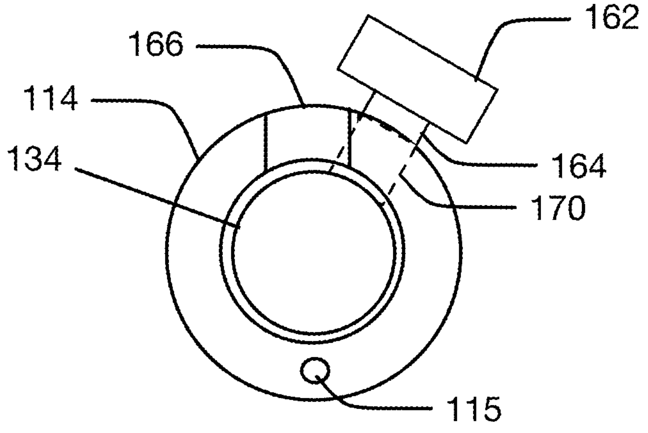
FIG. 7 is a diagrammatic proximal end view of the cautery tool and knife position-setting structure of the surgical instrument of FIG. 5, in accordance with the first embodiment of the present invention.

FIGS. 5-7 show a surgical instrument 110 in accordance with an embodiment of the present invention. Like parts are given the same part number. The surgical instrument 110 includes a cautery tool 18, an elongated body 114, a knife tool 20, and a proximal base 126. The cautery tool 8 includes a conductor 15 and a cautery tip 18. The cautery tip 18 may be embodied in various shapes, including but not limited to the ball, spatula, and hook configurations of FIGS. 2A-B, 3A-B, and 4A-C. The elongated body 114 has a channel 116, which preferably extends through the elongated body 114 from a proximal end to a distal end. The cautery tip 18 has a through opening 19 axially aligned with the channel 116. The cautery tip 18 is formed separate from the elongated body 114, and is removably attached and replaceable, or is permanently affixed. The conductor 15 is electrically coupled to the cautery tip 18. The knife tool 20, as shown in FIG. 5, includes a shaft 22 and a distal portion 24. The distal portion 24 has a cutting edge 25. The knife tool 20 is situated in the channel 16, and is movable between a retracted position and a fully extended position.

The surgical instrument 110 includes a proximal base 126 to which the elongated body 114 is removably attached by a connector 128. The proximal base 126 may serve as a handle for holding the surgical instrument 110 or be an adapter for coupling the surgical instrument 110 to a robotic arm. For example, the proximal base 126 may be a longitudinally-oriented hand grip generally aligned with the axis of the elongated body 14. Alternatively, the proximal base 126 may have one or more finger grips (such as of the shape used for scissors.) A power interface 130 is situated at the proximal base 126. A power source 32 is coupled to the power interface 130 to drive the cautery tool 12 into an active state, in which the cautery tip 18 is heated for performing a cauterizing action, such as to provide coagulation of a blood vessel, dissection of tissue, or destruction of tissue. A switch (not shown) at the power source turns power on or off to use the instrument 110 in the cautery-off state or cautery-on state. In some embodiments the power source includes batteries situated in the proximal base 26. A switch (not shown) is situated at the proximal base 26 and turns power on or off to use the instrument 110 in the cautery-off state or cautery-on state.

The knife position-setting structure 34 (FIG. 1) in the embodiment of FIGS. 5-8 is formed by a sled 134 and groove 166. The sled 134 includes a rigid, longitudinal portion 167 that is situated in the channel 116 of the elongated body 114. In one embodiment the distal end of the longitudinal portion 167 is fixedly or removably coupled to the proximal end of the shaft 22 of the knife tool 20. In another embodiment the longitudinal portion 167 and the shaft 22 are the same unitary structure formed as a single member. The longitudinal portion 167 and the knife tool 20 have a loose fit within the channel 116 allowing the sled 134 to move the knife tool 20 along the channel 116 forward or backward in an axial direction. The sled 134 also includes an access portion 161 formed by a knob 162 in communication with the longitudinal portion 167 by a radial arm 164. The access portion 161 preferably is located toward a proximal end of the sled 134, although in other embodiments the access portion 161 may be positioned anywhere along the sled 134. In one embodiment the access portion 161 and longitudinal portion 167 are a unitary structure formed as a single member. In other embodiments the access portion 161 is removably coupled to the longitudinal portion, such as by a threaded coupling in which the radial arm 164 screws into a threaded radial opening in the longitudinal portion 167. In one embodiment the sled 134 and knife tool 20 are a unitary structure formed as a single member.

As shown in FIGS. 5 and 6, the groove 166 is located at the proximal end of the elongated body 114. The access portion 161 runs along the groove 166. In particular the radial arm 164 extends radially from the longitudinal portion 167 in the channel 116 through the groove 166 to the knob 162. In the illustrated embodiment a plurality of circumferentially extending notches 170 are formed at respective locations along the groove 166. FIG. 6 shows three notches 170A, 170B, and 170C in the groove 166 of elongated body 114. The longitudinal portion 167 of the sled 134 along with the shaft 22 of the knife tool 20 have a circular cross section and have a loose fit in the channel 116. The longitudinal portion 167 of the sled 134 along with the shaft 22 of the knife tool 20 are able to rotate circumferentially within the channel 116 when the access portion 161 of sled 134 is aligned with any of the notches 170. When the access portion 161 is positioned along the longitudinally extending portions of the groove 166 not in circumferential alignment with a notch 170, circumferential rotation of the knife tool 20 is blocked. Specifically, the radial arm 164 is blocked by longitudinally extending walls of the groove 166, thereby preventing circumferential rotation of the longitudinal portion 167 and knife tool 20.

To lock the knife tool 20 in the retracted position (see FIGS. 2A, 3A, 4A) the access portion 161 (see FIG. 5) is positioned at notch 170A (see FIG. 6). In particular, the sled 134 is rotated circumferentially while the radial arm 164 is aligned with the notch 170A. The radial arm 164 is moved into the notch 170A, such as shown in FIG. 7. In some embodiments the radial arm 164 has a tight fit with the notch 170A (or the entryway of the notch 170A) thereby preventing the sled 134 from incidentally rotating once the radial arm 164 is positioned in the notch 170A. In other embodiments a separate locking mechanism may be included (not shown), which for example locks the radial arm in the notch 170A.

To move the knife tool 20 out of the retracted position, the surgeon grabs the access portion 161 and rotates the sled 134 circumferentially to move the radial arm 164 out of the notch 170A into the longitudinally extending portion of the groove 166. To move the knife tool 20 to the fully extended position (see FIGS. 2B, 3B, and 4B), the surgeon-gripping the knob 162—advances the access portion 161 along the groove 166 moving the sled 134 and knife tool 20 axially in the distal direction. The distal portion 24 of the knife tool 20 is advanced along the channel 116 and through the cautery tip's through channel 19 exposing the cutting edge 25 beyond the distal end of the cautery tip's through channel 19. To lock the knife tool 20 in the fully extended position (see FIGS. 2B, 3B, 4C) the access portion 161 (see FIG. 5) is positioned at notch 170C (see FIG. 6). In particular, the sled 134 is rotated circumferentially while the radial arm 164 is aligned with the notch 170C. The radial arm 164 is moved into the notch 170C, (See FIG. 7). In some embodiments the radial arm 164 has a tight fit with the notch 170C (or the entryway of the notch 170C) thereby preventing the sled 134 from incidentally rotating once the radial arm 164 is positioned in the notch 170C. In other embodiments a separate locking mechanism may be included (not shown), which for example locks the radial arm in the notch 170C. To move the knife tool 20 out of the fully extended position, the surgeon grabs the access portion 162 and rotates the sled 134 circumferentially to move the radial arm 162 out of the notch 170C into the longitudinally extending portion of the groove 166. The surgeon while still gripping the knob 162 moves the access portion 162, and thus the sled 134 and knife tool 20, axially in the proximal direction so as to return the knife tool to the retracted position. As already described, the access portion 161 may be positioned at notch 170A to lock the knife tool 20 in the retracted position.

For the ball 18' and spatula 18" embodiments of the surgical instrument 110 the notch 170B may be omitted. In such embodiments, the knife tool 20 is moved between a retracted position and a fully extended position. (See FIGS. 2A-2B and 3A-3B.) For the L-hook 18''' embodiment or other embodiments having an open space region 45 between the distal end of the channel 16 and proximal beginning of the cautery tip through opening 19''', one or more notches 170B may be included along the groove 166 corresponding to one or more respective intermediate extended positions of the knife tool 20, as described above with regard to FIGS. 4A-4C. To move the knife tool 20 out of any of the retracted position, intermediate extended position(s), and fully extended positions the surgeon grabs the access portion 162 and rotates the sled 134 circumferentially to move the radial arm 162 out of the corresponding notch 170 into the longitudinally extending portion of the groove 166. The surgeon gripping the knob 162 then moves the access portion 161, along with the sled 134 and knife tool 20, forwards or backwards in the axial direction to reposition the knife tool 20 into another position among the retracted position, intermediate extended position(s), and fully extended position.

Embodiments with 2Nd Knife Position-Setting Structure

FIGS. 8-13 show a surgical instrument 210 in accordance with another embodiment of the present invention. Like parts are given the same part number. The surgical instrument 210 includes an elongated body 14, a cautery tool 12, a knife tool 20, and a proximal base 226.

Figure 8:
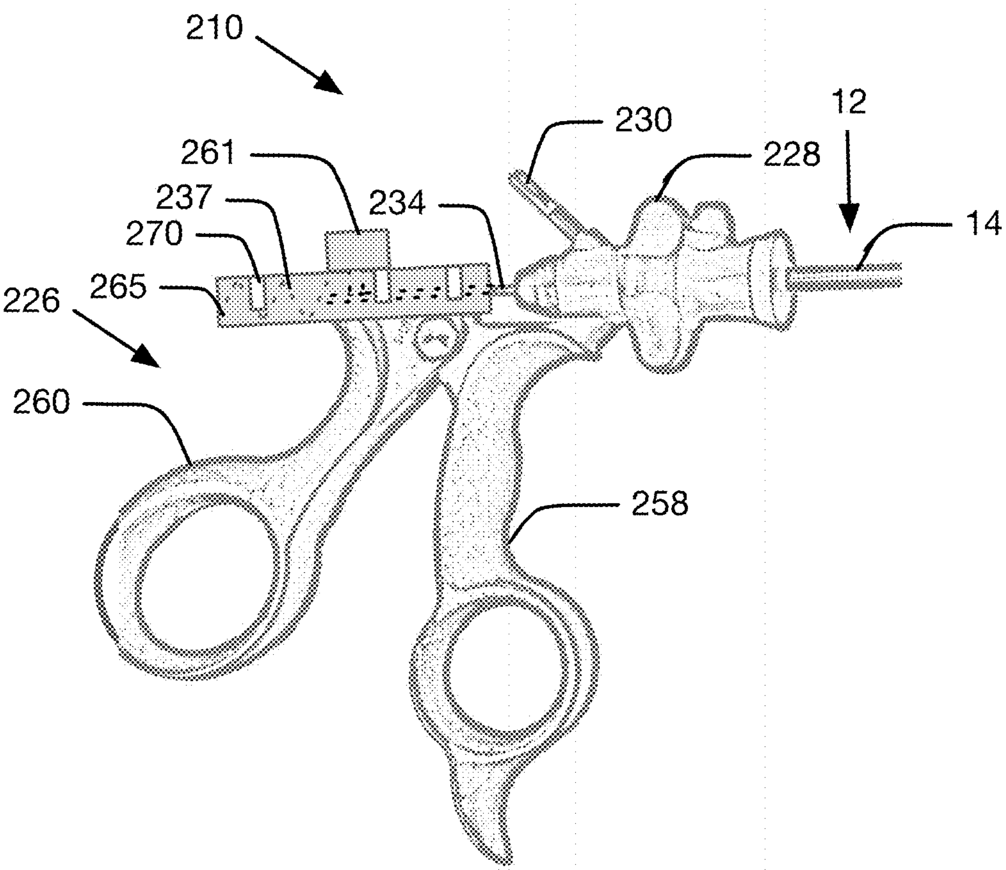
FIG. 8 is a perspective view of a proximal portion of a hand-held surgical instrument, in accordance with a second embodiment of the present invention.

The proximal base 226 may serve as a handle for holding the surgical instrument 210 or be an adapter for coupling the surgical instrument 210 to a robotic arm. For example, the proximal base 226 may be a longitudinally-oriented hand grip generally aligned with the axis of the elongated body 14. Alternatively, as shown in FIG. 8 the proximal base 226 includes a first grip 258, a second grip 260, and a body portion 265.

Figure 9:
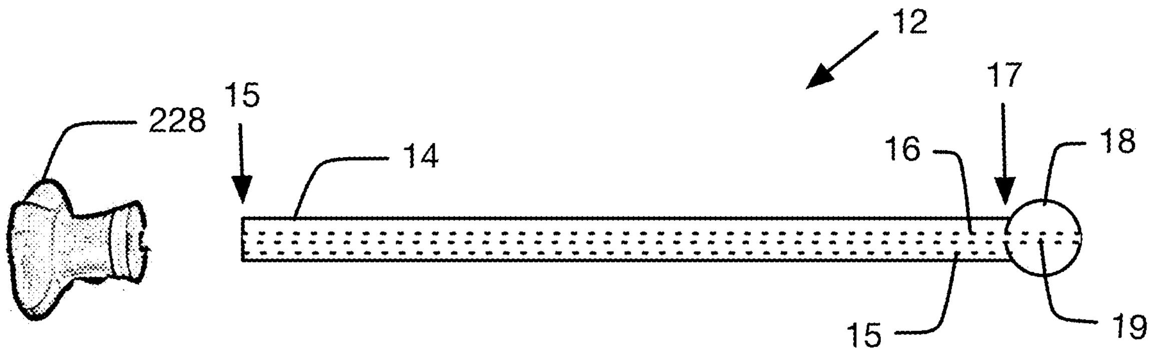
FIG. 9 is a perspective view of the connector and cautery tool of the surgical instrument, in accordance with a second embodiment of the present invention.
Figure 10:
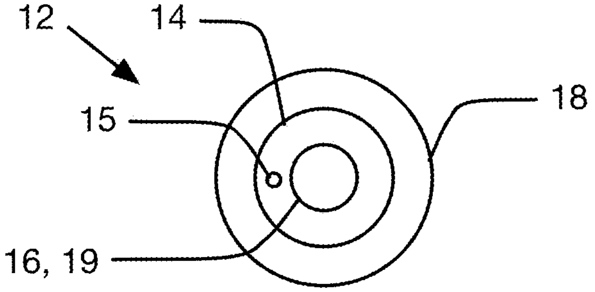
FIG. 10 is a diagrammatic distal end view of the cautery tool of the surgical instrument of FIG. 8, in accordance with the second embodiment of the present invention.
Figure 11:
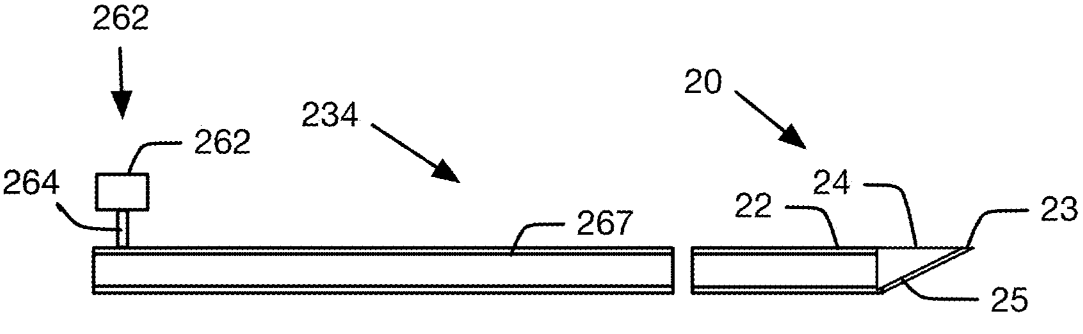
FIG. 11 is an exploded view of the knife tool and sled of the surgical instrument, in accordance with the second embodiment of the present invention.

As shown in FIG. 9, the cautery tool 12 includes a conductor 15 and a cautery tip 18. The cautery tip 18 may be embodied in various shapes, including but not limited to the ball, spatula, and hook configurations of FIGS. 2A-B, 3A-B, and 4A-C. The elongated body 14 has a channel 16, which preferably extends through the elongated body 14 from a proximal end 13 to a distal end 17. The cautery tip 18 has a through opening 19 axially aligned with the channel 16. The cautery tip 18 is formed separately from the elongated body 14 and is removably attached and replaceable, or is permanently affixed. The knife tool 20, as shown in FIG. 11, includes a shaft 22 and a distal portion 24. The distal portion 24 has a cutting edge 25. The knife tool 20 is situated in the channel 16, and is movable between a retracted position and a fully extended position.

The elongated body 14 is removably attached to the proximal base 226 by the connector 228. A power interface 230 is situated at the proximal base 226 and extends through the connector 228 to be in electrical communication with the elongated body 14. A power source 32 (FIG. 1) is coupled to the power interface 230 to drive the cautery tool 12 into an active state, in which the cautery tip 18 is heated for performing a cauterizing action, such as to provide coagulation of a blood vessel, dissection of tissue, or destruction of tissue. A switch (not shown) at the power source turns power on or off to use the instrument 210 in the cautery-off state or cautery-on state. In some embodiments the power source includes batteries situated in the proximal base 226. A switch (not shown) is situated at the proximal base 226 and turns power on or off to use the instrument 210 in the cautery-off state or cautery-on state.

Figure 12:
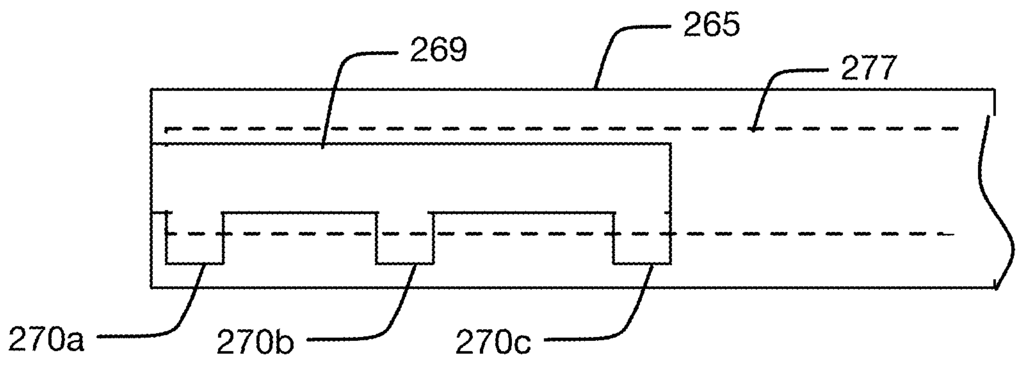
FIG. 12 is a diagrammatic view of the body, body groove and channel of the base portion of the surgical instrument, in accordance with the second embodiment of the present invention.

The knife position-setting structure 34 (FIG. 1) in the embodiment of FIGS. 8-13 is formed by a sled 234 and a body portion groove 269 (see FIGS. 11 and 12.) The groove 269 is formed in the body portion 265 of the proximal base 226. The body portion groove 269 is radially continuous with a channel 277 within the body portion 265. In one embodiment the body portion groove 269 is narrower in the transverse direction than the maximum diameter of the channel 277. In another embodiment the body portion groove 269 width in the transverse direction is the same as the maximum diameter of the channel 277. The sled 234 has the same construction and alternative embodiments as for the sled 134 described with regard to the surgical instrument 110 embodiments. However, the sled 234 extends further in the proximal direction, so as to extend proximally into the body portion 265 of the proximal base 226. The sled 234 includes a rigid, longitudinal portion 267 that extends within the channel 277 of the body portion 265 and the channel 16 of the elongated body 14 to the knife tool's shaft 22. The longitudinal portion 267 and the knife tool 20 have a loose fit within the channel 16 allowing the sled 234 to move the knife tool 20 along the channel 277 and channel 16 forward or backward in an axial direction. The sled 234 extends from the knife tool 20 along the channel 16 proximal to the proximal end 13 of the elongated body 14 through the connector 226 into the body portion 265 of the proximal base 226 along channel 277. The sled 234 has an access portion 261 formed by a knob 262 in communication with the longitudinal portion 267 by ta radial arm 264. The access portion 261 is located toward a proximal end of the sled 234. In one embodiment the sled 234 and knife tool 20 are a unitary structure formed as a single member. In some embodiments the sled 234 is spring-biased in the proximal direction. For example, a spring 237 is coupled to the proximal end of the sled 234 and to a housing of the body 235. The surgeon overcomes the spring tension when moving the access portion 261 distally to advance the sled 234 along body portion groove 269.

The channel 277 is axially aligned with the channel 16 of the elongated body 14 and the through opening 19 of the cautery tip 18. The proximal end of the sled 234 is situated in the channel 277. The body portion groove 269 is of similar shape as the groove 166 in the elongated body 114 of the surgical instrument 110 embodiment. The body portion groove 269 extends in the axial direction at the periphery of the body portion 265, and is in radial communication with the channel 277. In the illustrated embodiment a plurality of circumferentially extending notches 270 are formed at respective locations along the body portion groove 269. FIG. 12 shows three notches 270A, 270B, and 270C along the body portion groove 269. The longitudinal portion 267 of the sled 234 along with the shaft 22 of the knife tool 20 have a circular cross section and have a loose fit in the channels 16 and 277. The longitudinal portion 267 of the sled 234 along with the shaft 22 of the knife tool 20 are able to rotate circumferentially within the channel 16 when the access portion 261 of sled 234 is aligned with any of the notches 270. When the access portion 261 is positioned along the longitudinally extending portions of the body portion groove 269 not in circumferential alignment with a notch 270, circumferential rotation of the knife tool 20 is blocked. Specifically, the radial arm 264 is blocked by longitudinally extending walls of the body portion groove 269, thereby preventing circumferential rotation of the longitudinal portion 267 and knife tool 20.

Figure 13:
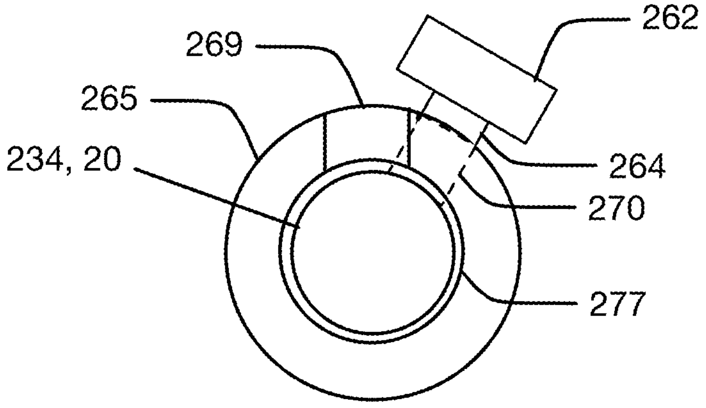
FIG. 13 is a diagrammatic proximal end view of the body, body groove and channel of the base portion of the surgical instrument, in accordance with the second embodiment of the present invention.

Movement of the knife tool 20 between the retracted position and fully extended position is the same as described above for the surgical instrument embodiment 110. In particular, the action between the access portion 261 and body portion groove 269 and notches 270 of FIGS. 12 and 13 is the same as the action between the access portion 161 and groove 166 and notches 170 of FIGS. 6 and 7 for the surgical instrument 110 embodiment. To move the knife tool 20 out of any of the locked positions (i.e., retracted position, intermediate extended position, and fully extended position), the surgeon grabs the access portion 261 and rotates the sled 234 circumferentially to move the radial arm 264 out of the corresponding notch 270 into the longitudinally extending portion of the body portion groove 269. The surgeon gripping the knob portion 262 then moves the access portion 261, along with the sled 234 and knife tool 20, forwards or backwards in the axial direction to reposition the knife tool 20 into another position. The knife tool 20 is locked into a position by the radial arm 264 of the sled 234 being situated in a notch 270.

For the ball 18' and spatula 18'' embodiments of the surgical instrument 210 the notch 270B may be omitted. In such embodiments, the knife tool 20 is moved between a retracted position and a fully extended position. (See FIGS. 2A-2B and 3A-3B.) For the L-hook 18''' embodiment or other embodiments having an open space region 45 between the distal end of the channel 16 and proximal beginning of the cautery tip through opening 19, one or more notches 270B may be included along the body portion groove 269 corresponding to one or more respective intermediate extended positions of the knife tool 20, as described above with regard to FIGS. 4A-4C. To move the knife tool 20 out of any of such positions, the surgeon grabs the access portion 261 and rotates the sled 234 circumferentially to move the radial arm 264 out of the corresponding notch 270 into the longitudinally extending portion of the body portion groove 269. The surgeon gripping the knob portion 262 then moves the access portion 261, along with the sled 234 and knife tool 20, forwards or backwards in the axial direction to reposition the knife tool 20 into another position among the retracted position, intermediate extended position(s), and fully extended position. The knife tool 20 is locked into a position by the radial arm 264 of the sled 234 being situated in a notch 270.

In an alternative embodiment, the body portion groove 269 does not have any notches, and the access portion 261 is not rotated circumferentially. Instead, the body portion 265 also includes a notched lid member (not shown) which covers all or portion(s) of the body portion groove 269. The lid member is rotated in a circumferential direction (or hinged to lift off the groove 269) to expose the entire length of the body portion groove 269. The sled 234 is moved along the body portion groove 269 forward or backward in the axial direction to position the radial arm 264 into circumferential alignment with a notch in the lid member. The lid member then is rotated in the reverse circumferential direction (or hinged to return onto the groove 269) to cover the body portion groove 269. As covered, at least a portion of the groove 269 proximal to and distal to the notch 270 is covered. In some embodiments only the groove 269 portions aligned with the notched portions of the lid member are exposed, but with the radial arm 264 extending radially through one of the notches. Accordingly, the knife tool 20 is locked into a position corresponding to the aligned notch. Each notch corresponds to a given retracted or extended position of the knife tool 20.

Embodiments with 3Rd Knife Position-Setting Structure

Figure 14:
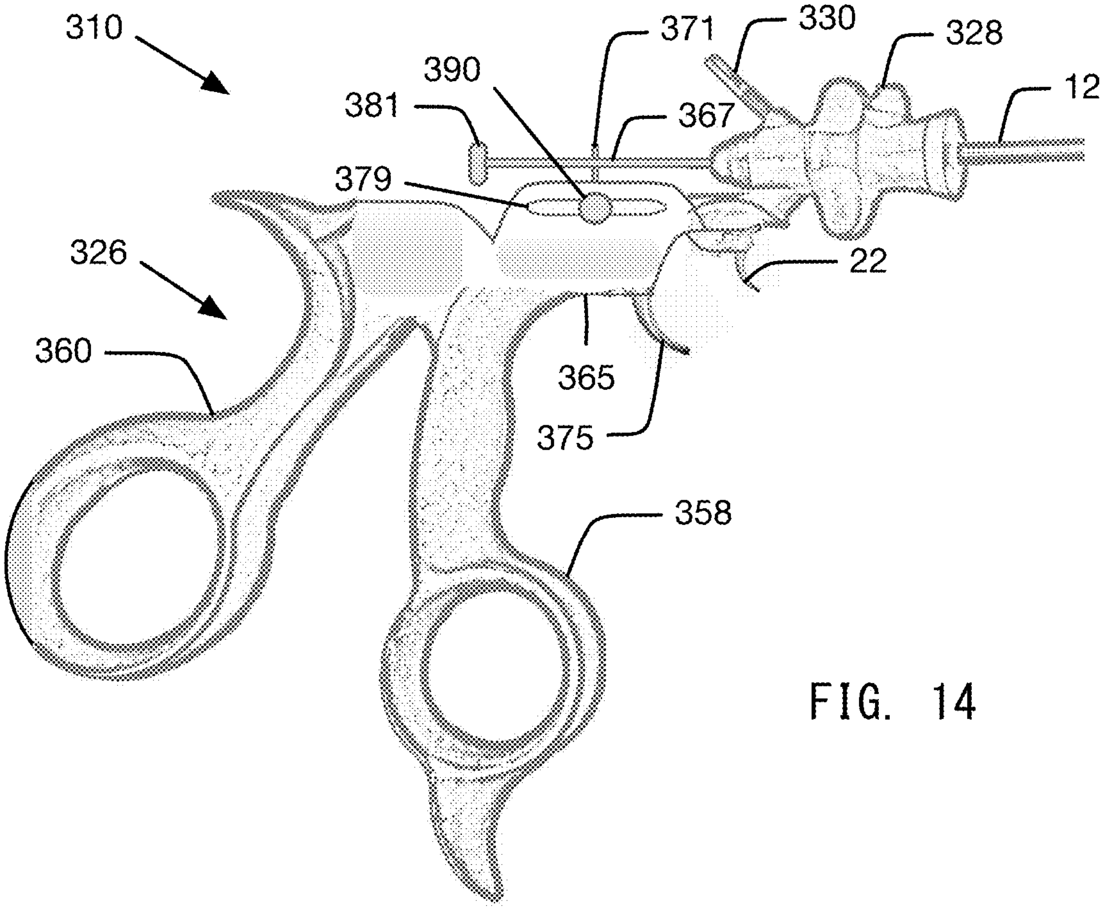
FIG. 14 is a perspective view of a proximal portion of a hand-held surgical instrument, in accordance with a third embodiment of the present invention.
Figure 15:
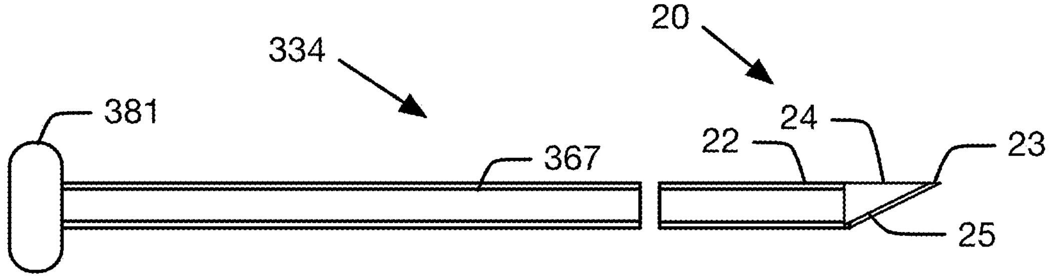
FIG. 15 is an exploded view of the knife tool and sled of the surgical ins
Figure 16:
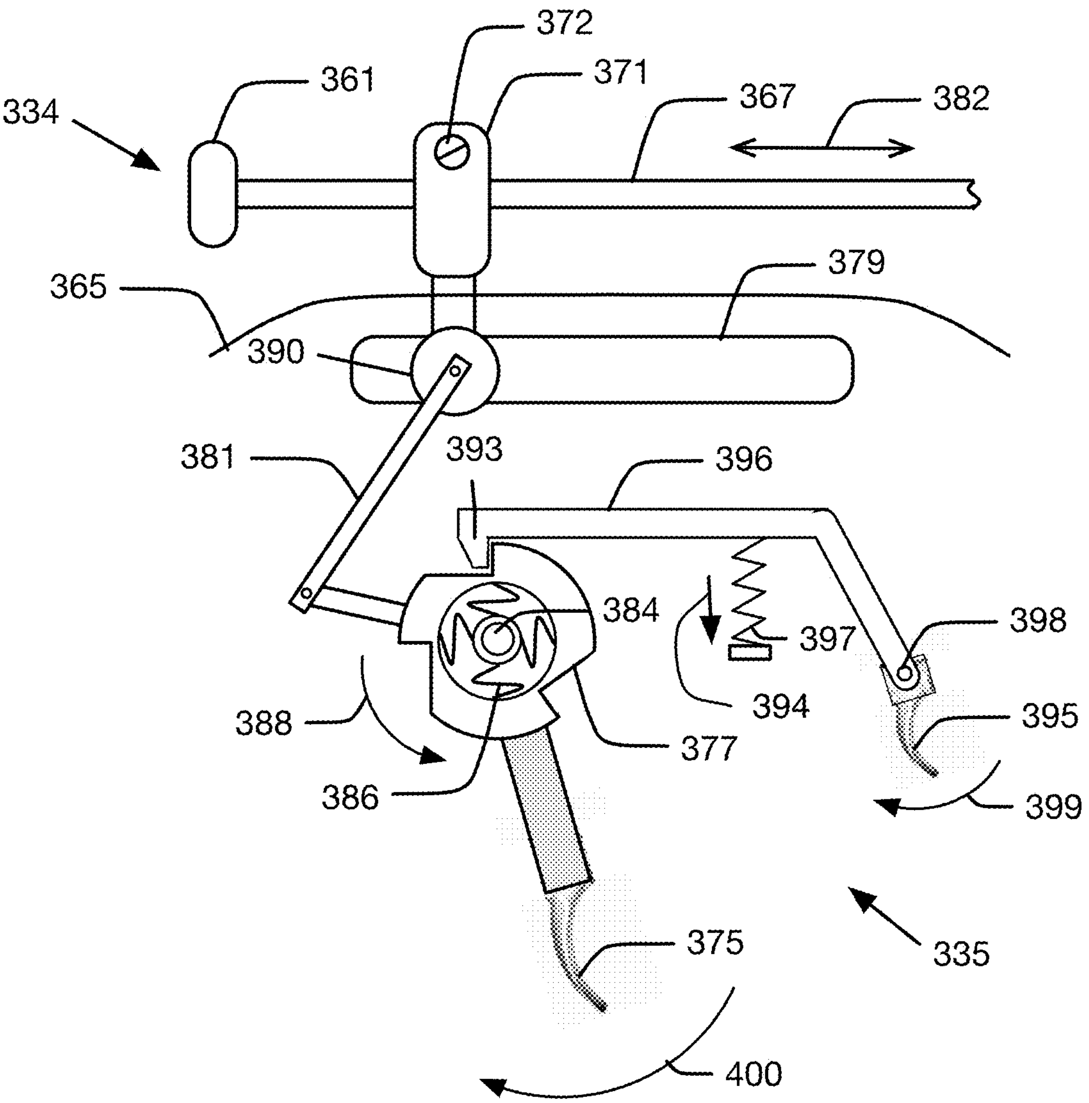
FIG. 16 is a schematic view of the knife position-setting structures including a sled and a ratchet, pawl and trigger mechanism, in accordance with the third embodiment of the present invention.

FIGS. 14-16 show a surgical instrument 310 in accordance with another embodiment of the present invention. Like parts are given the same part number. The surgical instrument 310 includes an elongated body 14, a cautery tool 12, a knife tool 20, and a proximal base 326.

The proximal base 326 may serve as a handle for holding the surgical instrument 310. For example, the proximal base 326 may be a longitudinally-oriented hand grip generally aligned with the axis of the elongated body 14. Alternatively, as shown in FIG. 14 the proximal base 326 includes a first grip 358, a second grip 360, and a body portion 365.

As shown in FIG. 9, the cautery tool 12 includes a conductor 15 and a cautery tip 18. The cautery tip 18 may be embodied in various shapes, including but not limited to the ball, spatula, and hook configurations of FIGS. 2A-B, 3A-B, and 4A-C. The elongated body 14 has a channel 16, which extends through the elongated body 14 from a proximal end 13 to a distal end 17. The cautery tip 18 has a through opening 19 axially aligned with the channel 16. The cautery tip 18 is formed separately from the elongated body and is removably attached and replaceable, or is permanently affixed. The knife tool 20, as shown in FIG. 15, includes a shaft 22 and a distal portion 24. The distal portion 24 has a cutting edge 25. The knife tool 20 is situated in the channel 16, and is movable between a retracted position and a fully extended position.

The cautery tool 12 is removably attached to the proximal base 326 by the connector 328. In particular the elongated body 14 is coupled to the connector 328. A power interface 330 is situated at the proximal base 326 and extends through the connector 328 to be in electrical communication with the elongated body 14. A power source 32 (FIG. 1) is coupled to the power interface 330 to drive the cautery tool 12 into an active state, in which the cautery tip 18 is heated for performing a cauterizing action, such as to provide coagulation of a blood vessel, dissection of tissue, or destruction of tissue. A switch (not shown) at the power source turns power on or off to use the instrument 310 in the cautery-off state or cautery-on state. In other embodiments the power source includes batteries situated in the proximal base 326. A switch (not shown) is situated at the proximal base 326 and turns power on or off to use the instrument 310 in the cautery-off state or cautery-on state.

The knife position-setting structure 34 (FIG. 1) in the embodiment of FIGS. 14-16 is formed by a sled 334 and a ratchet, pawl and trigger mechanism 335 (see FIG. 16) situated in the body portion 365. For a longitudinal hand grip embodiment in which the hand grip is generally aligned with the axis of the elongated body 14, the ratchet, pawl and trigger mechanism 335 are situated in the longitudinal hand grip (which serves as the body portion 365.)

The sled 334 includes a rigid, longitudinal portion 367 that extends through the connector 328 into the channel 16 of the elongated body 14 to the knife tool's shaft 22. The longitudinal portion 367 and the knife tool 20 have a loose fit within the channel 16 allowing the sled 334 to move the knife tool 20 along the channel 16 forward or backward in an axial direction. The sled 334 has an access knob 361 attached or integral to the proximal end of the longitudinal portion 367. In one embodiment the sled 334 and knife tool 20 are a unitary structure formed as a single member.

Referring to FIG. 16, in an exemplary embodiment the longitudinal portion 367 of sled 334 is coupled to the ratchet, pawl and trigger mechanism 335 by a coupling member 371. When loose, the coupling member 371 allows for the sled 334 to be positioned relative the coupling member 371 at a desired position along the longitudinal length of the sled 334. When locked, such as by a screw 372 threaded into the coupling member 371 to tighten the grip on the longitudinal portion 367, the sled 334 is fixed relative to the coupling member 371. The coupling member 371, in effect, allows one to calibrate the fully extended position of the knife tool 20, so that the distal end 23 of the knife tool extends a desired distance beyond the through hole 19 of the cautery tip 18.

The ratchet, pawl and trigger mechanism 335, as shown in FIG. 16, includes a first trigger 375, a ratchet gear 377, a track 379, and one or more link members 381 for coupling to the sled 334 to advance the sled 334 forward in the axial direction 382 along the channel 16. In some embodiments one or more additional gears 384 are included to provide a gear ratio greater than 1:1 for the translation of motion of first trigger 375 to axial motion of the sled 334 and knife tool 20. A spring 386 biases the ratchet gear 377 and first trigger 375 in a direction 388 to return the sled 334 and knife tool 20 into the retracted position (see FIGS. 2A, 3A, and 4A) along channel 16.

One of the link member(s) 381 is coupled to a wheel 390 that runs along the track 379. The coupling member 371 is coupled to the wheel 390, so that as the wheel 390 moves along the track 379, the coupling member 371 moves the sled 334 in a corresponding axial movement.

Referring to FIG. 16, in an exemplary embodiment the ratchet, pawl and trigger mechanism 335 also includes a pawl 393 and second trigger 395. A spring 397 biases the pawl 393 in direction 394 into physical engagement with the ratchet gear 377. The pawl 393 includes an arm portion 396 that is fixedly coupled to an axle 398. The second trigger 395 also is fixedly coupled to the axle 398. As the second trigger 395 in moved in direction 399 about an axis defined by axle 398, the pawl 393 is lifted out of engagement with the ratchet gear 377. Such lack of engagement causes the spring 386 associated with the ratchet gear 377 to force the ratchet gear 377 to rotate in direction 388 returning the first trigger 375, sled 334 and knife tool 20 back to a position where the knife tool 20 is in the retracted position.

The position of the first trigger 375 defines the axial position of distal tip 23 of the knife tool 20. When the trigger 375 is pulled in direction 400 the ratchet gear 377 is rotated directly or via one or more gears 384 in a direction opposite direction 388. As per ratchet and pawl design, the ratchet gear 377 is able to be moved in the direction opposite direction 388 without being restricted by the pawl 393. Accordingly, the surgeon pulls the first trigger 375 to rotate the ratchet gear 377 into a position corresponding to an intermediate extended position (see FIG. 4B) or a fully extended position (see FIGS. 2B, 3B, and 4C) of the knife tool 20. The pawl is spring biased to engage each ratchet of the ratchet gear 277. The number of ratchets the pawl 393 can travel over the full distance the first trigger 375 can be pulled corresponds to the number of discrete positions at which the knife tool 20 can be locked. The various ratchets along the circumference of the ratchet gear 377 thus correspond to the retracted position, zero or more respective intermediate positions, and the fully extended position of the knife tool 20. When the first trigger 375 is released the pawl 393 locks the ratchet gear 377 and correspondingly the sled 334 and knife tool 20 into position.

When the first trigger 375 is pulled, the ratchet gear 377 rotates forcing the link member(s) 381 to move the wheel 390 along the track 379 forward in the axial direction 382. While the first trigger 375 is not forced by the surgeon, and the second trigger 395 is pulled in direction 399, the ratchet gear 377 rotates in direction 388 forcing the link member(s) 381 to move the wheel 390 along the track 379 backward in the axial direction 382. Forward motion corresponds to advancement of the sled 334 and knife tool 20 distally. Backward motion corresponds to retraction of the sled 334 and knife tool 20 proximally.

Materials and Other Embodiments

The surgical instrument embodiments described above are for use by a medical practitioner performing a medical procedure. The instrument is particularly adapted for minimally invasive surgery, including robotic-assisted surgery. For embodiments intended for multiple procedures, the instruments described herein are designed for easy assembly and disassembly, for sterilization, and for stability during use. The instruments can be sterilized using any medically acceptable method. In some instances, the entire instrument is sterilized. In other instances, after the surgical procedure, the proximal base components and knife position-setting structure can be sterilized and re-used, while the elongated body, cautery tool and knife tool are discarded. In still other instances, only the cautery tip and/or knife tool are discarded and the rest sterilized and re-used.

As shown in FIGS. 5, 8, and 45, the proximal base 126, 226, 326 can be a longitudinal hand grip along the same general axis as the elongated body, a robotic arm adapter, a hand grip having a first finger grip and second finger grip, or a hand grip having a first finger grip, second finger grip, and body portion. The longitudinal hand grip in some embodiments has contours for the fingers of the surgeon to align along the grip. The hand grips having finger grips, can include first and second finger openings sized to receive the surgeon's fingers. The finger openings can be elongated and sized to receive one or more of the surgeon's fingers during the procedure. One of the grips may include an opening for one finger and a contoured unenclosed profile for other fingers. The first grip, second grip, and body portion may be formed as one or more members. The longitudinal hand grip, and the first grip, second grip and body portion can be formed of any medical grade metal, such as stainless steel, or any medical grade polymer so long as the material has sufficient properties to carry out the functions described herein. If the surgical instrument is reusable, then the grips are constructed from a medical grade metal or polymer that can be appropriately sterilized.

In preferred embodiments the elongated body is made from an electrically insulative material, such as a medical grade polymer having sufficient properties to carry out the functions described herein. If the surgical instrument is reusable, then the elongated body is constructed from a medical grade polymer that can be appropriately sterilized.

In preferred embodiments the conductor is made of a conductive metal or alloy satisfying physiological requirements. In preferred embodiments the cautery tip is made of silver, tungsten steel, or other stable metal or alloy satisfying physiological requirements and possessing the desired ohmic resistance, so that the tip may directly constitute an electric heating or resistance element. In some embodiment the cautery tip includes a coating formed of platinum, palladium or another suitable metal or alloy.

Figure 17:
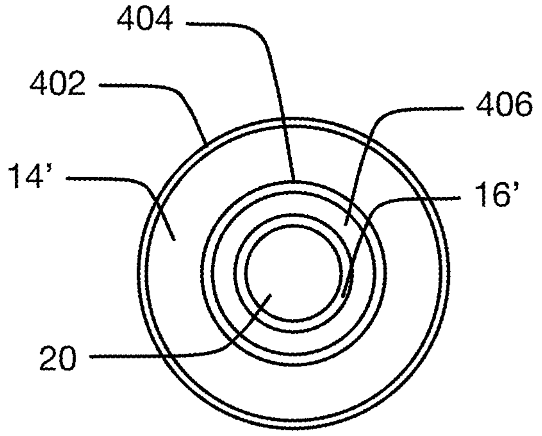
FIG. 17 is a diagrammatic cross sectional view of the elongated body and knife tool, in accordance with an alternative embodiment of the present invention.

In an alternative embodiment as shown in FIG. 17, the elongated body 14' is formed by a conductive material and serves as the conductor for the cautery tip. The conductive elongated body 14' and cautery tip may for formed as a single member with the elongated body being an electrode, and the cautery tip being a conductive element. For such an embodiment the elongated body 14' preferably has a polytetrafluoroethylene (PTFE) coating 402, 404 along the external surface and lining the channel 16' through which the knife tool 20 moves. Alternatively, another insulative coating satisfying physiological and thermal requirements may be used or further provided. In some embodiments an insulative sleeve 406 is included in the channel 16' of the conductive elongated body 14', such as shown in FIG. 17. The sleeve 406 does not move relative to the elongated body 14' and is made of an electrically insulative and thermally insulative material capable of meeting physiological and temperature constraints. The knife tool moves within the sleeve 406. The PTFE coating 404, 404 or other coating is an insulator, preferably withstanding flaking at high temperatures, and resists eschar buildup during surgical procedures. In some embodiments for the conductive elongated body 14', a longitudinally extending insulation grip (not shown) is positioned along at least a portion of the length of the elongated body. The cautery tip is free from the PTFE coating 404, 404, insulative sleeve 406, and other insulation, so as to maximize the heating effect at the cautery tip.

In some embodiments, the knife tool 20 and sled 34, 134, 234, 334 are made of steel or another metal or alloy satisfying physiological requirements. The knife tool 20 and sled 34, 134, 234, 334 also include a PTFE coating or other insulative coating. Preferably only the cutting edge of the knife tool 20 is left uncoated, so as to provide an effective cutting edge. In other embodiments, the sled 34, 134, 234, 334 is made of a rigid insulative material, satisfying physiological requirements. In other embodiments the knife tool 20 and/or sled 34, 134, 234, 334 is made from a polymer or other electrically insulative material capable of maintaining a sharp cutting edge under exposure to cautery tip heating temperatures, while also satisfying physiological and thermal requirements.

In preferred embodiments, the cutting capability of the knife tool is limited to (consists of) one cutting member which cuts using a mechanical action to apply physical stresses. The knife tool is distinguished from an electrical cutting edge, which applies electrical current or heat to cut. The knife tool is distinguished from surgical scissors. Surgical scissors consist of two members arranged so that at least one member, coupled to the other at a pivot point, moves relative to the other to achieve a cutting action. A pin provided as the pivot point couples the two members. For scissors respective blades may slide across each other. For surgical scissors, one member may move relative to the second member with one member having a cutting edge, and the second member serving an anvil, flat edge, or a second cutting edge. In contrast, the knife tool embodiments illustrated herein lack a second member coupled to the shaft or distal portion at a pivot point. There is no second member coupled to and pivotally movable relative to the shaft, distal portion, or the cutting edge, which acts together with the cutting edge to perform a cutting action. The knife tool has no pivot point along the shaft or distal portion shared by a crossing blade, a second cutting edge member, flat edge member, or anvil member. In a preferred embodiment there is no capability for pivotally moving the cutting edge relative to the shaft or distal portion of the knife tool In the illustrated surgical tool embodiment the knife tool is limited to axial motion (i.e., forward and backward motion along the axis) and rotational motion (i.e., about the axis), referenced to the axis of the channel in which the knife tool is situated. In the illustrated surgical tool embodiment there is no capability for an off-axis motion of any portion of the knife tool relative to the axis of the channel in which the knife tool is situated. The cutting edge is sharp enough to cut through tissue without a being referenced to or butting against a second surgical cutting edge member, a surgical flat edge member, or a surgical anvil member. In some embodiments, the distal portion has multiple cutting edges on one member such as in a spear shaped distal portion.

The invention is intended to extend to all functionally equivalent structures, methods and uses, such as are within the scope of the appended claims. Those skilled in the art, having the benefit of the teachings of this specification, may affect numerous modifications thereto and changes may be made in form and details without departing from the scope and spirit of the invention.

What is claimed:

1. A surgical instrument for performing multiple operative actions, the instrument comprising:

an elongated body extending longitudinally in an axial direction and having a first channel extending in the longitudinal direction to a distal end of the elongated body;

a knife tool including a shaft and a distal portion having a blade, the knife tool being situated in the first channel and movable along the first channel, the blade for performing a cutting action consisting of mechanically cutting by applying physical stress, the blade having a cutting edge with a physical sharpness adapted for performing the cutting action against tissue; and a cautery tool including a conductor and a cautery tip, the cautery tip positioned at the distal end of the elongated body in electrical communication with the conductor, the cautery tip having a through hole in axial alignment with the first channel;

wherein the cautery tip has a cautery-off state and a cautery-active state, during the cautery-active state the cautery tip being energized to provide heat for performing any one or more of a cauterizing, coagulating, and dissecting action;

wherein the knife tool has a retracted position in which the blade of the knife tool is unexposed, and a fully extended position in which at least a portion of the blade is exposed distal to the through opening to perform the cutting action; and wherein the cautery tip is configured as a hook having a ledge portion and the cautery tip through hole extends through the ledge portion.

2. The surgical instrument of claim 1, wherein the elongated body is rigid and nonconductive, and has a second channel in which the conductor is located.

3. The surgical instrument of claim 1, wherein the elongated body comprises the conductor and an insulative coating, the first channel lined with the insulative coating.

4. The surgical instrument of claim 1, further comprising means for moving the knife tool along the first channel between the retracted position and the fully extended position, the knife tool being stably positioned when in the retracted position and being stably positioned when in the fully extended position.

5. The surgical instrument of claim 1, further comprising a position-setting member formed by a track along which an access structure is accessible, the access structure being movable along the track, the access structure being coupled to the knife tool, wherein movement of the access structure relative to the track causes movement of the knife tool along the first channel, the access structure having a first locked position corresponding to the knife tool in the retracted position and having a second locked position corresponding to the knife tool in the fully extended position.

6. The surgical instrument of claim 5, wherein the track is formed as a groove in the elongated body.

7. The surgical instrument of claim 5, further comprising a proximal base;

wherein the elongated body is coupled to the proximal base, and the first channel is a through channel; and wherein the track is formed in the proximal base.

8. The surgical instrument of claim 1, further comprising a robotic arm, and wherein the elongated body is coupled to the robotic arm by a connector.

9. A surgical instrument for performing multiple operative actions, the instrument comprising:

an elongated body extending longitudinally in an axial direction and having a first channel extending in the longitudinal direction to a distal end of the elongated body;

a knife tool including a shaft and a distal portion having a blade, the knife tool being situated in the first channel and movable along the first channel, the blade for performing a cutting action consisting of mechanically cutting by applying physical stress, the blade having a cutting edge with a physical sharpness adapted for performing the cutting action against tissue; and a cautery tool including a conductor and a cautery tip, the cautery tip positioned at the distal end of the elongated body in electrical communication with the conductor, the cautery tip having a through hole in axial alignment with the first channel;

wherein the cautery tip has a cautery-off state and a cautery-active state, during the cautery-active state the cautery tip being energized to provide heat for performing any one or more of a cauterizing, coagulating, and dissecting action;

wherein the knife tool has a retracted position in which the blade of the knife tool is unexposed, and a fully extended position in which at least a portion of the blade is exposed distal to the through opening to perform the cutting action; and further comprising:

a proximal base, to which the elongated body is coupled, the proximal base having a track;

an elongated member continuous with the shaft of the knife tool; and a coupling member coupling the elongated member to the track, in which movement of the coupling member along the track translates to axial motion of the elongated member and knife tool.

10. The surgical instrument of claim 9, further comprising:

a first trigger, a ratchet gear, and pawl together configured to move the coupling member along the track when the first trigger is pulled, and further configured to lock the knife tool in an axial position relative to the first channel.

11. The surgical instrument of claim 10, further comprising:

a second trigger for releasing the pawl from the ratchet gear to unlock the knife tool from a current position and allow the knife tool to be retracted along the first channel.

12. The surgical instrument of claim 11, wherein the ratchet gear is spring biased to move the coupling member along the track in a proximal direction when the pawl releases the ratchet gear, so as to return the knife tool to the retracted position.

13. The surgical instrument of claim 9, wherein the cautery tip is configured as a spatula.

14. The surgical instrument of claim 9, wherein the cautery tip is configured in a ball shape.

15. The surgical instrument of claim 9, wherein the cautery tip is configured as a hook having a ledge portion and the cautery tip through hole extends through the ledge portion.

16. The surgical instrument of claim 1, wherein the knife tool further has an intermediate position at which at least a portion of the cutting edge is exposed in an open space region between a distal end of the first channel and a proximal end of the through opening, so as to allow cutting of tissue captured at a proximal side of the ledge portion.

17. The surgical instrument of claim 1, wherein the knife tool has only one blade and wherein the one blade is configured to apply physical stress to cut tissue mechanically without requiring an anvil or scissor cutting method.

18. The surgical instrument of claim 1, wherein the cautery tip has an ohmic resistance element configured to perform thermal electrocauterization.

19. A surgical instrument for performing multiple operative actions, the instrument comprising:

an elongated body extending longitudinally in an axial direction and having a first channel extending in the longitudinal direction to a distal end of the elongated body;

a knife tool including a shaft and a distal portion having a blade, the knife tool being situated in the first channel and movable along the first channel, the blade for performing a cutting action consisting of mechanically cutting by applying physical stress, the blade having a cutting edge with a physical sharpness adapted for performing the cutting action against tissue; and a cautery tool including a conductor and a cautery hook having a ledge portion, the cautery hook positioned at the distal end of the elongated body in electrical communication with the conductor, the ledge portion having a through hole in axial alignment with the first channel, an open space region occurring between a distal end of the channel and a proximal end of the through hole;

wherein the cautery hook has a cautery-off state and a cautery-active state, during the cautery-active state the cautery hook being energized to provide heat for performing any one or more of a cauterizing, coagulating, and dissecting action; and wherein the knife tool has a retracted position in which the blade of the knife tool is unexposed, a fully extended position in which at least a portion of the blade is exposed distal to the through hole to perform the cutting action on tissue at a distal side of the ledge portion, and an intermediate position at which at least a portion of the cutting edge is exposed in the open space region to perform the cutting action on tissue captured at a proximal side of the ledge portion.

20. The surgical instrument of claim 19, further comprising means for moving the knife tool along the first channel between the retracted position, the intermediate position, and the fully extended position, the knife tool being stably positioned when in the retracted position, being stably positioned when in the intermediate position, and being stably positioned when in the fully extended position.

* * * * *